United States Patent
Isono et al.

(10) Patent No.: US 8,530,202 B2
(45) Date of Patent: Sep. 10, 2013

(54) BETA-1,3-GLUCAN MANUFACTURING METHOD

(75) Inventors: Naoto Isono, Tsu (JP); Yutaka Yamamoto, Tsu (JP); Wataru Saburi, Fuji (JP)

(73) Assignee: Mie University, Tsu-Shi (JP)

( * ) Notice: Subject to any disclaimer, the term of this patent is extended or adjusted under 35 U.S.C. 154(b) by 0 days.

(21) Appl. No.: 13/148,844

(22) PCT Filed: Feb. 11, 2010

(86) PCT No.: PCT/JP2010/052001
§ 371 (c)(1),
(2), (4) Date: Aug. 10, 2011

(87) PCT Pub. No.: WO2010/092997
PCT Pub. Date: Aug. 19, 2010

(65) Prior Publication Data
US 2011/0319609 A1    Dec. 29, 2011

(30) Foreign Application Priority Data
Feb. 11, 2009   (JP) ................... 2009-029185

(51) Int. Cl.
*C12P 19/04*    (2006.01)
(52) U.S. Cl.
USPC .......................................................... 435/101
(58) Field of Classification Search
None
See application file for complete search history.

(56) References Cited

FOREIGN PATENT DOCUMENTS

| | | |
|---|---|---|
| JP | 4-066092 | 3/1992 |
| JP | 6-113874 | 4/1994 |
| JP | 2001-299338 | 10/2001 |

OTHER PUBLICATIONS

Albrecht et al., Phytochemistry 10: 1293-1298 (1971).*
Kauss et al., Biochem. Biophys. Res. Comm. 35(6): 926-930 (1969).*
Klarzynski et al., Plant Physiol. 124: 1027-1037 (2000).*
Lienart et al., Plant Sci. 58: 165-170 (1988).*
Yamagishi et al., J. Phycol. 43: 519-527 (2007).*
International Search Report from parent PCT application No. PCT/JP2010/052001.
Bulone, V. et al., "In vitro synthesis of a microfibrillar (1,3)-beta-glucan by a ryegrass (*Lolium multiflorum*) endosperm (1,3)-beta-glucan synthase enriched by product entrapment", The Plant Journal, 1995, vol. 8(2), pp. 213-225.
Hrmova, M. et al., "Mutated Barley (1,3)-beta-D-Glucan Endohydrolases Synthesize Crystalline (1,3)-beta-D-Glucans", The Journal of Biological Chemistry, vol. 277, No. 33, Issue of Aug. 16, pp. 30102-30111 (2002).

(Continued)

*Primary Examiner* — Patricia A Leith
*Assistant Examiner* — Erin M Bowers
(74) *Attorney, Agent, or Firm* — J-Tek Law PLLC; Jeffrey D. Tekanic

(57) ABSTRACT

A method for manufacturing a linear-chain beta-1,3-glucan is disclosed that comprises polymerizing glucose-1-phosphate serving as a substrate by contacting the glucose-1-phosphate with a beta-1,3-glucan phosphorylase derived from a species in the genus *Ochromonas*. A laminarioligosaccharide may be added to serve as a primer. A linear-chain beta-1,3-glucan having a degree of polymerization between about 30 to 70 is also disclosed.

18 Claims, 5 Drawing Sheets

(56) References Cited

OTHER PUBLICATIONS

Sasaki, T. et al., "Dependence on Chain Length of Antitumor Activity of (1,3)-beta-D-Glucan from *Alcaligenes faecalis* var. *myxogenes*, IFO 13140, and Its Acid-degraded Products", Cancer Research, 38, pp. 379-383 (1978).

Kauss, H. et al., "Demonstration and partial purification of a beta-(1,3)-glucan phosphorylase", Biochem.Biophys.Res. Commun., 1969, vol. 35, No. 6, pp. 926-930.

Albrecht, G.J. et al., "Purification, crystallization, and properties of a beta-(1,3)-glucan phosphorylase from *Ochromonas malhamensis*", Phytochemistry, 1971, vol. 10, No. 6, pp. 1293-1298.

Yutaka Yamamoto et al., "*Ochromonas danica* Yurai beta-1,3-glucan phosphorylase no Seisei to Shoseishitsu Kaiseki", Nippon Nogei Kagakukai Taikai Koen Yoshihsu, Mar. 5, 2009, vol. 2009, p. 48.

Yutaka Yamamoto et al., "Beta-1,3-glucan phosphorylase no Seisei to Shoseishitsu", J.Appl.Glycosci., Jul. 20, 2009, vol. 56, No. Suppl., p. 41.

Naoto Isono et al., "Phosphorylase o Mochiita beta-1,3-glucan no Gosei", J.Appl.Glycosci., Jul. 20, 2009, vol. 56, No. Suppl., p. 41.

Written Opinion from parent PCT application No. PCT/JP2010/052001, including English translation of prior art rejection.

English translation of International Preliminary Report on Patentability from parent PCT application No. PCT/JP2010/052001.

English translation of Yutaka Yamamoto et al., "*Ochromonas danica* Yurai beta-1,3-glucan phosphorylase no Seisei to Shoseishitsu Kaiseki", Nippon Nogei Kagakukai Taikai Koen Yoshihsu, Mar. 5, 2009, vol. 2009, p. 48.

English translation of Yutaka Yamamoto et al., "Beta-1,3-glucan phosphorylase no Seisei to Shoseishitsu", J.Appl. Glycosci., Jul. 20, 2009, vol. 56, No. Suppl., p. 41.

English translation of Naoto Isono et al., "Phosphorylase o Mochiita beta-1,3-glucan no Gosei", J.Appl.Glycosci., Jul. 20, 2009, vol. 56, No. Suppl., p. 41.

\* cited by examiner (ppm)

BETA-1,3-GLUCAN MANUFACTURING METHOD

CROSS-REFERENCE

This application is the U.S. national stage of International Patent Application No. PCT/JP2010/052001 filed on Feb. 11, 2010, which claims priority to Japanese Patent Application No. 2009-029185, filed on Feb. 11, 2009.

TECHNICAL FIELD

The present invention relates to a method of manufacturing beta-1,3-glucan.

BACKGROUND ART

Beta-1,3-glucan is a polysaccharide, in which glucoses extend via beta-1,3-type bonds. Beta-1,3-glucan is synthesized by fungi, algae, higher plants, bacteria, etc.; its molecular weight broadly ranges from several thousands to several million. Research and development of this substance have advanced since it has been recognized to have anti-bacterial and anti-viral activities, blood-clotting activity, anti-cancer activity, immune-modulating activity, etc. The potency of the activity of beta-1,3-glucan is known to differ depending upon the structure and molecular weight thereof; beta-1,3-glucan extracted from fungi, etc., cannot exhibit the desired activity as is.

Consequently, research and development have been performed for the purpose of manufacturing beta-1,3-glucan or a laminarioligosaccharide having a suitable molecular weight. For example, regarding the latter, a method of manufacturing a laminarioligosaccharide (degree of polymerization of 2~20) using an enzyme extracted from the cells of the genus *Euglena* is disclosed in Patent Document 1. A method of manufacturing a laminarioligosaccharide by reacting glucose with glucose-1-phosphate (G1P) using an enzyme extracted from the genus *Bacillus* is disclosed in Patent Document 2. A method of manufacturing a laminarioigosaccharide, which is characterized by reacting an *Euglena algal* body and/or *Euglena algal* body extract with a water-soluble beta-1,3-glucan, is disclosed in Patent Document 3.

PRIOR ART DOCUMENTS

Patent Documents

Patent Document 1: Publication No. H4-066092
Patent Document 2: Publication No. 2001-299338
Patent Document 3: Publication No. H6-113874

Non-Patent Literature

Non-Patent Literature 1: The Plant Journal, 1995, Vol. 8(2), pp. 213-225
Non-Patent Literature 2: The Journal of Biological Chemistry, Vo. 277, No. 33, Issue of August 16, pp. 30102-30111 (2002)
Non-Patent Literature 3: Cancer Research, 38, pp. 379-383 (1978)

SUMMARY OF THE INVENTION

In Non-Patent Literature 1, a method of manufacturing beta-1,3-glucan (degree of polymerization of 1,500) using beta-1,3-glucan synthase is disclosed. Although this method mimics a process of manufacturing beta-1,3-glucan in nature, it has the disadvantages that the UDP glucose used as the substrate is expensive and the beta-1,3-glucan synthase is difficult to handle since it is a membrane protein.

Furthermore, in Non-Patent Literature 2, a method of synthesizing beta-1,3-glucan (degree of polymerization of 30~34) according to a glycosynthase reaction that uses an organic chemical reaction and a hydrolase is disclosed. However, this method has the disadvantages that laminaribiose (one type of disaccharide that beta-1,3 links two glucose molecules), which is a raw material, is expensive and that complicated procedures are required to obtain the laminaribiose fluoride that will be used in the polymerization reaction.

On the other hand, in Non-Patent Literature 3, data have been reported that linear-chain beta-1,3-glucan having a degree of polymerization of 50~120 has a higher anti-tumor activity than curdlan produced by the soil bacterium, Agrobacterium, or a laminarioligosaccharide having a degree of polymerization less than 30. However, linear-chain beta-1,3-glucan having a degree of polymerization of 50~120 does not exist in nature, and it is difficult to prepare such beta-1,3-glucan in large quantities by a process of hydrolyzing curdlan, etc.

The present invention was made in view of the foregoing circumstances and its object is to provide a method that can manufacture beta-1,3-glucan comprising several tens of polymerized glucoses in a simple way.

The inventors discovered that beta-1,3-glucan can be manufactured by a polymerization reaction with glucose-1-phosphate (G1P) serving as a substrate, by using beta-1,3-glucan phosphorylase (EC 2.4.1.97) derived from the genus *Ochromonas*, which basically led to the completion of the invention.

Thus, a method of manufacturing beta-1,3-glucan according to the present invention is characterized by performing a polymerization reaction with glucose-1-phosphate serving as the substrate by using beta-1,3-glucan phosphorylase derived from the genus *Ochromonas*.

In the above-mentioned invention, it is preferred that the *Ochromonas* genus is *Ochromonas danica*.

Furthermore, the pH during the polymerization reaction is preferably 4~8.

Furthermore, the concentration of the glucose-1-phosphate during the polymerization reaction is preferably 0.01 M~0.6 M (more preferably, 0.1 M~0.5 M).

Furthermore, it is preferred that the beta-1,3-glucan phosphorylase is extracted from cells of the genus *Ochromonas*, and it is purified to such a degree that the addition of a primer is not required during the manufacture of the beta-1,3-glucan. The primer is a substance that is primarily utilized by beta-1,3-glucan phosphorylase when producing beta-1,3-glucan by a polymerization reaction with G1P serving as the substrate; for example, a laminarioligosaccharide, etc., such as laminaribiose, can be used.

Furthermore, the temperature during the polymerization reaction is preferably 20° C.~45° C. In a method of the present invention, the degree of glucose polymerization of the product can be suitably varied by controlling the temperature during the reaction. For example, the degree of glucose polymerization is about 50~60 in a low temperature range (20° C.~25° C.), about 60~70 in an intermediate temperature range (26° C.~37° C.) and about 40~60 in a high temperature range (38° C.~45° C.). Accordingly, a product with a suitable degree of polymerization can be obtained by controlling the temperature during the reaction.

*Ochromonas* is a microalgae belonging to the Chrysophyceae of the Heterokontophyta; it has one or two flagella of unequal length and swims independently. The shape is a spherical, oval, elliptical, etc. and no conspicuous structure, such as chaeta, can be found on the cell surface. Furthermore, the cell does not have a shell but has chloroplasts of yellow, yellow-brown, bister, dark yellow-green, etc. The *Ochromonas* genus includes the species of *Ochromonas danica, Ochromonas tuberculata, Ochromonas malhamensis*, etc. *Ochromonas danica* is preferably used in the present invention, although any species can be used.

Beta-1,3-glucan phosphorylase is an enzyme that catalyzes a phosphorolysis reaction, which liberates a glucose residue (G1P) linked at the beta-(1→3)-bond from a non-reducing end of the beta-1,3-glucan. Since the reaction is reversible, beta-1,3-glucan can be produced when the concentration of G1P is higher than a certain value. However, because the optimal conditions (pH, temperature, G1P concentration, etc.) in the manufacture of beta-1,3-glucan from G1P differ depending upon the characteristics of the beta-1,3-glucan phosphorylase, which is produced by an organism serving as the supply source, the optimal conditions need to be individually considered.

The beta-1,3-glucan phosphorylase used in the invention can be used in any one of (1) a state of a suspension liquid of disrupted cells (a cell-free extract), (2) a partially purified state after cell disruption (crude enzyme), and (3) a highly purified state (highly-purified enzyme). From among these, it is preferred to use the enzyme in state (2) or (3). In order to purify the enzyme, it is preferred to perform (A) a cell disruption step of disrupting the cells, (B) a centrifuge separation step of precipitating and removing cell fragments, (C) a protein purification step of precipitating the protein by adding a salt (e.g., ammonium sulfate) to the protein contained in the supernatant, and after dissolving this precipitate in a suitable buffer, performing a dialysis treatment, and (D) a chromatography step of separating and purifying the dialyzed solution by utilizing appropriate chromatography (column chromatography, thin-layer chromatography, high performance liquid chromatography (HPLC), supercritical fluid chromatography, ion chromatography, affinity chromatography, paper chromatography, etc.; and partition chromatography, adsorption chromatography, molecular-exclusion chromatography, ion-exchange chromatography, gel filtration, etc.).

When beta-1,3-glucan phosphorylase is used in the above state (2) (crude enzyme), it is preferable that the beta-1,3-glucan phosphorylase is purified to such a degree that beta-1,3-glucan can be produced without the addition of a laminarioligosaccharide that serves as a primer for the synthesis reaction with G1P as the substrate. Since it can be understood that the crude enzyme contains a component that synthesizes a primer when it is mixed with G1P, by including this substance in advance, beta-1,3-glucan can easily be manufactured without the addition of a laminarioligosaccharide as a primer. However, when the crude enzyme is used, beta-1,3-glucan may be colored (browning) by another impurity. Accordingly, when using a crude enzyme, it is preferred to use a suitable reducing agent. For example, dithiothreitol (DTT), 2-mercaptoethanol, tris (2-carboxyethyl)phosphine (TCEP), glutathione, ascorbic acid, etc. are given as examples of such reducing agents.

Furthermore, when beta-1,3-glucan phosphorylase is used in the above state (3) (highly-purified enzyme), it is preferred that a laminarioligosaccharide, such as laminaribiose, is used as a primer in the polymerization reaction.

Furthermore, as the buffer used in the polymerization reaction, for example and without limitation, it can be suitably selected from a citrate buffer solution, an acetate buffer solution, an MES-sodium-hydrate buffer solution, a PIPES-sodium-hydrate buffer solution, an MOPS-sodium-hydrate buffer solution, an HEPES-sodium-hydrate buffer solution, a tris-HCl buffer solution, etc. From among these, the citrate buffer solution, the acetate buffer solution and the MES-sodium-hydrate buffer solution are more preferable.

According to the present invention, beta-1,3-glucan having several tens (about 30 to 70) of polymerized glucoses can easily be manufactured.

MODES FOR CARRYING OUT THE INVENTION

Figure 1:
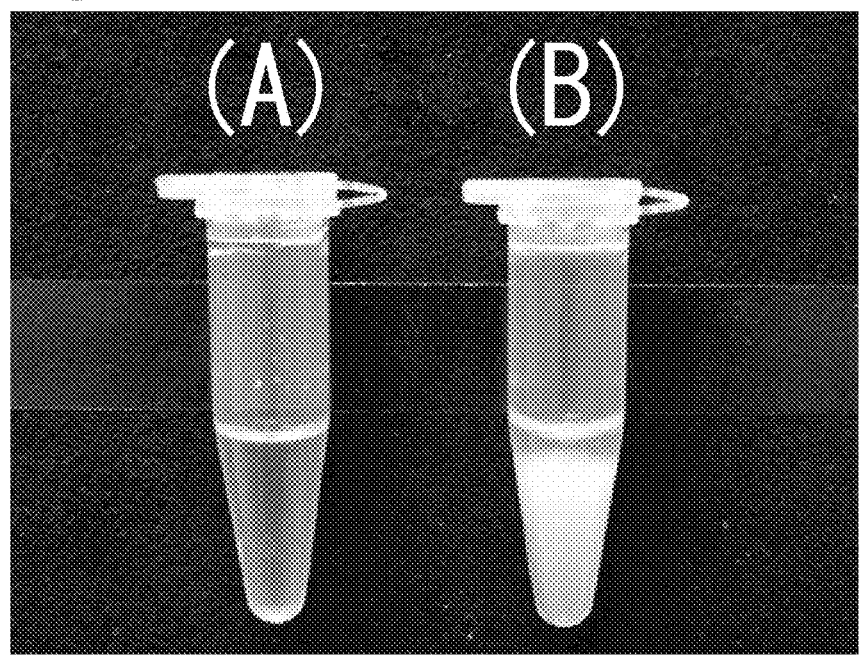
FIG. 1 is a photograph taken at a time that confirmed the state of forming the precipitate when the crude enzyme was used. The left side (A) shows the reaction solution before the reaction, and the right side (B) shows the reaction solution after the passage of 24 hours. Precipitation of polysaccharide was observed in (B).

Embodiments according to the invention will be described with reference to the drawings and tables. However, the technical scope of the invention should not be limited to the embodiments, as the invention can be practiced in various modes without changing the scope of the invention. Furthermore, the technical scope of the invention covers the scope of equivalence.

<Materials and Methods>

1. Culture of *Ochromonas Danica*

*Ochromonas danica* was sold in lots by the Microbial Culture Collection of the National Institute for Environmental Studies.

A suspension of *O. danica* was added to 250 mL of culture medium that contained 1 g/L polypeptone (Nacalai Tesque), 1 g/L of dry yeast extract (Nacalai Tesque), 0.5 g/L of meat extract (Remel) and 1 g/L of glucose and a seed culture was carried out at 22° C. without shaking in cycles of a 12-hour light period and a 12-hour dark period. The culture fluid (250 mL) was added to 5.0 L of culture medium that contained 5 g/L of peptone (Mikuni Chemical Industries Co., Ltd.), 2 g/L of dry yeast extract and 15 g/L of glucose and it was cultured with shaking at 30° C. at 120 rpm for three days. No exposure to light was carried out.

After culturing, centrifuge separation (6,000×g, 10 minutes, 4° C.) was carried out and the cells were collected. After suspending the cells in 250 mL of distilled water (4° C.), centrifuge separation (6,000×g, 10 minutes, 4° C.) was carried out and the supernatant was removed. After repeating this rinsing operation three times, it was stored at −30° C. until used.

2. Purification of beta 1,3-glucan phosphorylase

After suspending the cells obtained in 1 above in 250 mL of buffer solution A (20 mM Tris, 1 mM. EDTA and 1 mM DTT, pH 8.0), they were disrupted using an ultrasonic generator (UD-201, Tomy Seiko). The disruption was performed under the conditions of OUTPUT 4, DUTY 40 and 5 minutes while cooling with ice water (algal body disrupting step). Subsequently, centrifuge separation (40,000×g, 30 minutes, 4° C.) was carried out and the supernatant was collected (centrifuge separation step).

Ammonium sulfate was added to the obtained supernatant so that a 30% saturated concentration was achieved. It was left at 4° C. for one hour, centrifuge separation (10,000×g, 15 minutes, 4° C.) was carried out and the supernatant was collected. Ammonium sulfate was added to this so that a 70% saturated concentration was achieved. It was left at 4° C. for one hour, centrifuge separation (10,000×g, 15 minutes, 4° C.) was carried out and the supernatant was removed. After dissolving the obtained precipitate in 10 mL of buffer solution A, dialysis was carried out against 1 L of buffer solution A at 4° C. for 16 hours (protein purification step).

The solution after dialysis was subjected to Q Sepharose Fast Flow (ϕ1.6 cm×20 cm, GE Healthcare) that equilibrated using the buffer solution A. After addition of the solution and sufficiently washing using the buffer solution A, protein was eluted using a linear concentration gradient (120 minutes) of 0 M to 1 M sodium chloride. All operations were carried out at a flow rate of 5 mL/min and 5 mL fractions were collected (chromatography step). Activity measurements were carried out using a portion of the obtained fractions. Fractions having higher activity were collected and defined as the crude enzyme. The crude enzyme was frozen in liquid nitrogen and stored at −80° C. until used.

In order to obtain an enzyme having a higher degree of purification, the following purification was further carried out. Ammonium sulfate was added to the crude enzyme so that a 30% saturated concentration was obtained. This solution was subjected to HiTrap Phenyl HP (5 mL, GE Healthcare) that equilibrated using the buffer solution A containing 30%-saturated ammonium sulfate. After addition of the sample and sufficiently washing the column using the buffer solution A, protein was eluted using a linear concentration gradient (250 mL) of 30% to 0% ammonium sulfate and using 50 mL buffer solution A. All operations were carried out at a flow rate of 5 mL/min and 5 mL fractions were collected.

Fractions having higher enzyme activity were collected and dialyzed at 4° C. for 16 hours against 2 L of buffer solution B (20 mM Tris, 1 mM DTT, pH 7.5). The dialyzed solution was subjected to RESOURCE Q (1 mL, GE Healthcare) that equilibrated using the buffer solution B. After addition of the sample and sufficiently washing the column using the buffer solution B, protein was eluted using a linear concentration gradient of 0 to 190 mM sodium chloride (10 mL) and a linear concentration gradient of 190 to 230 mM sodium chloride (200 mL). All operations were carried out at a flow rate of 1 mL/min and 1 mL fractions were collected. Fractions having higher enzyme activity were collected and defined as highly-purified enzyme. The highly-purified enzyme was stored at 4° C. until used.

3. Activity Measurement of beta-1,3-glucan phosphorylase

50 μL of 0.2 M sodium citrate buffer solution (pH 5.5), 10 μL of 100 mM glucose-1-phosphate (G1P, Wako Pure Chemical Industries) and 20 μL of 5 mM laminaripentaose (Seikagaku Biobusiness) were mixed together. After preincubation at 30° C. for 10 minutes, 20 μL of enzyme solution was added to the mixture and it was maintained at 30° C. for 10 minutes. In order to determine the amount of inorganic phosphate that was produced, 1000 μL of molybdenum reagent [15 mM ammonium molybdate, 100 mM zinc acetate (pH 5.0)] and 250 μL of ascorbic acid reagent [10% (w/v) ascorbic acid (pH 5.0)] were added to the reaction solution, it was maintained at 30° C. for 15 minutes, and OD850 was measured using a spectrophotometer. The amount of enzyme that produced 1 μmol inorganic phosphate in 1 minute was defined as 1 U. Furthermore, the protein concentration was determined according to the method of Bradford, Analytical Biochemistry, 72, 248-254 (1976).

4. Enzymatic Synthesis of Polysaccharide

250 μL of 0.2 M citrate buffer solution (pH 5.5), 100 μL of 0.5 M G1P, 150 μL of the crude enzyme (3.45 U/mg, 2.13 U/mL) and 0.5 μL of 1 M dithiothreitol were mixed together and maintained at 30° C. for 24 hours. In this case, primer, such as laminarioligosaccharide, etc., was not added. After the reaction, centrifuge separation (5000×g, 5 minutes) was carried out and the precipitate was collected. After suspending this in 1 mL of distilled water, centrifuge separation (5000×g, 5 minutes) was carried out and the supernatant was removed. After further repeating this rinsing operation twice, water was removed by lyophilization.

5. Analysis of the Precipitate

The measurement of the total amount of sugar was performed according to the phenol-sulfuric acid method (Dubois et al., Analytical Chemistry, 29, 350-356 (1956)).

The molecular weight distribution of the precipitate was analyzed by size-exclusion chromatography. TSKgel α-3000 (ϕ0.78 cm×30 cm, Toso) was used as the column. The precipitated sample, which was dissolved in 80% dimethylsulfoxide (DMSO), was applied to the column. 80% DMSO containing 10 mM sodium nitrate was used as the eluting solution, the separation was carried out at flow rate of 0.3 mL/min and a column temperature of 40° C. and detection was carried out using a differential refractive index detector. Agilent 1100 (manufactured by Agilent Technologies) was used as the HPLC system. In addition, Pullulan (Showa Denko) was used as the molecular weight standards.

A sugar composition analysis was carried out according to the method of Blakeney et al., Carbohydrate Research, 113, 291-299 (1983).

The type of bonds between the monosaccharide residues was determined by methylation analysis and nuclear magnetic resonance analysis (NMR analysis). The methylation analysis was carried out according to the methods of Ciucanu and Kerek, Carbohydrate Research, 131, 209-217 (1984) and Harris et al., Carbohydrate Research, 127, 59-73 (1984). GC-MS (GCMS-QP2010, Shimadzu Corporation) was used for the separation and analysis of partially methylated alditol acetates. SP-2380 (30 m×25 mm×0.2 µm, Supelco) was used as the column. Helium was used as the carrier gas, the pressure was 150 kPa and the split ratio was 100. The temperature of the vaporizing chamber was set to 275° C., and 1 µL of the sample was applied. After maintaining the temperature of the column oven at 70° C. for 4 minutes, it was increased to 150° C. at a gradient of 25° C./min. Subsequently, the column oven temperature was increased to 220° C. at a gradient of 4° C./min and maintained at 220° C. for 5 minutes. The column oven temperature was then increased to 270° C. at a gradient of 25° C. and maintained at 270° C. for 5 minutes. The mass spectrum was recorded in the EI mode. The temperature of the ion source was set to 200° C., the temperature of the interface was set to 250° C., the scan start time was set to 10 minutes, the termination time was set to 34.7 minutes and the scanning range of m/z ranged from 35 to 350. In addition, the precipitate was dissolved in DMSO-d6 so as to achieve 10 mg/mL, and the nuclear magnetic resonance spectrum of $^{13}C$ was observed using a nuclear magnetic resonance apparatus (JEOL, JNM-A500). The number of integrations was set to 15,000, and DMSO-d6 (39.5 ppm) was used as the internal standard. Furthermore, the nuclear magnetic resonance spectrum of curdlan having beta-1,3-glucoside bonds was also observed in the same manner.

6. Synthesis of beta-1,3-glucan Using Highly-Purified Enzyme

200 µL of 1 M citrate buffer solution (pH 5.5), 100 µL of 0.5 M G1P, 600 µL of highly-purified enzyme (15.3 U/mg, 0.46 U/mL) and 5 µL of 1 M dithiothreitol were mixed together. 100 µL of distilled water or 10 mM of laminaripentaose (primer) was further added to the mixture and it was maintained at 30° C. for 24 hours.

7. Analysis of the Influence of the Reaction Temperature

250 µL of 0.2 M citrate buffer solution (pH 5.5), 100 µL of 0.5 M G1P, 150 µL of crude enzyme (4.82 U/mg, 1.35 U/mL) and 2.5 µL of 1 M dithiothreitol were mixed together and maintained for 24 hours at a suitable temperature within the range of 20° C.~55° C. In this case, primer, such as laminarioligosaccharide, was not added. After the reaction, centrifuge separation (5000×g, 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

Furthermore, the produced beta-1,3-glucan was subjected to size-exclusion chromatography and the molecular weight of the beta-1,3-glucan was estimated from the position of the elution peak. Moreover, the conditions of the size-exclusion chromatography were the same as those described in <5. Analysis of the precipitate>.

8. Analysis of the Influence of pH

250 µL of 0.2 M citrate buffer solution (adjusted to a suitable pH within the range of 3.9~7.3), 100 µL of 0.5 M G1P, 150 µL of crude enzyme (4.82 U/mg, 1.35 U/mL) and 2.5 µL of 1 M dithiothreitol were mixed together and maintained at 30° C. for 24 hours. In this case, primer, such as laminarioligosaccharide, was not added. After the reaction, centrifuge separation (5000×g, 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

Furthermore, the produced beta-1,3-glucan was subjected to size-exclusion chromatography and the molecular weight of the beta-1,3-glucan was estimated from the position of the elution peak. Moreover, the conditions of the size-exclusion chromatography were the same as those described in <5. Analysis of the precipitate>.

9. Analysis of the Influence of G1P Concentration

50 µL of 1 M citrate buffer solution (pH 5.5), 250 µL of G1P (a suitable concentration within the range of 20 mM~800 mM), 150 µL of crude enzyme (4.82 U/mg, 1.35 U/mL) and 2.5 µL of 1 M dithiothreitol were mixed together and maintained at 30° C. for 24 hours. In this case, primer, such as laminarioligosaccharide, was not added. After the reaction, centrifuge separation (5000×g, 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

Furthermore, the produced beta-1,3-glucan was subjected to size-exclusion chromatography and the molecular weight of beta-1,3-glucan was estimated from the position of the elution peak. Moreover, the conditions of the size-exclusion chromatography were the same as those described in <5. Analysis of the precipitate>.

10. Analysis of the Influence of the Amount of Enzyme

100 µL of 1 M acetate buffer solution (pH 5.5), 100 µL of 0.5 M G1P and crude enzyme (2.56 U/mg, 1.28 U/mL, a suitable amount within the range of 0.02 U~1.0 U) were mixed together. 10 µL of distilled water or 50 mg/mL of laminarioligosaccharide (primer) was further added to the mixture and the total volume was adjusted to 500 µL with distilled water. The laminarioligosaccharide was prepared by hydrolyzing laminarin (Nakalai Tesque) by using Zymolyase 20T (Seikagaku Biobusiness). The above-described reaction solution was maintained at 30° C. for 48 hours. After the reaction, centrifuge separation (5000×g, for 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

11. Analysis of the Influence of the Amount of Primer

100 µL of 1 M acetate buffer solution (pH 5.5), 100 µL of 0.5 M G1P and a suitable amount of 0.02 U crude enzyme (2.56 U/mg, 1.28 U/mL) were mixed together. Furthermore, a suitable amount of laminarioligosaccharide (primer) within the range of 0~2 mg/mL was added to the mixture and the total volume was adjusted to 500 µL with distilled water. The above-mentioned reaction solution was maintained at 30° C. for 48 hours. After termination of the reaction, centrifuge separation (5000×g, 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

12. Analysis of the Influence of the G1P Concentration when Primer is Added 1 mg/mL of laminarioligosaccharide (primer), a suitable amount of G1P within the range of 0.05 M~0.6 M and 1 U/g-ds crude enzyme (2.56 U/mg, 1.28 U/mL) were mixed together and the total volume was adjusted to 500 μL with 0.25 M acetate buffer solution (pH 5.5). This reaction solution was maintained at 30° C. for 48 hours. After the reaction, centrifuge separation (5000×g, 5 minutes) was carried out and the precipitate was collected. After suspending the precipitate in 1 mL of distilled water, centrifuge separation (5000×g, 5 minutes) was carried out and the supernatant was removed. This rinsing operation was further repeated twice. The weight of the beta-1,3-glucan obtained as the precipitate was determined by the phenol-sulfuric acid method, and the product yield was calculated.

<Experimental Results>

1. Production of the Precipitate

The precipitate was produced when crude enzyme and G1P were reacted with each other in the citrate buffer solution (pH 5.5) as shown in FIG. 1. Precipitate was not produced when the same reaction was performed without either the enzyme or G1P. Furthermore, precipitate was not produced when the same reaction was performed using inactivated enzyme that had been previously heated at 100° C. for 5 minutes. Accordingly, it was inferred that the phenomenon of producing precipitate is an enzyme reaction that depends upon G1P.

2. Characteristics of the Precipitate

The precipitate did not dissolve in cold water, ethanol, acetone, or 1 M hydrochloric acid. Furthermore, based upon visual observation, the precipitate dissolved in 1 M sodium hydroxide or 80% dimethyl sulfoxide (DMSO). Although the precipitate dissolved in hot water (100° C.), the precipitate formed again when cooled. Based upon these data, it became clear that the precipitate has characteristics, which are often observed in water-insoluble polysaccharides.

The weight of the precipitate was 6.1±0.2 mg when the reaction was carried out in the 0.5 mL system. Furthermore, the total sugar amount measured by the phenol-sulfuric acid method was 6.0±0.2 mg (glucose equivalents). Based upon this, it became clear that the majority of the precipitate is comprised of sugar. Furthermore, since the amount of sugar added to the reaction system was 9.0 mg (glucose equivalents), the yield of the precipitate was calculated to be not less than 60%.

3. Molecular Weight Distribution of the Precipitate

The precipitate was dissolved in 80% DMSO; when analyzed by size-exclusion chromatography, the elution position was between Pullulan P-10 (estimated molecular weight of 12,200) and Pullulan P-5 (estimated molecular weight of 5,800) (TABLE 1). Based upon a regression analysis of the molecular weight and elution time, the sample comprising the precipitate was estimated to have a molecular weight distribution with a peak in the vicinity of the molecular weight of about 11,400 (degree of glucose polymerization about 70). Accordingly, the main component of the precipitate was considered to be polysaccharide.

TABLE 1

Analysis of the molecular weight distribution of the precipitate by size-exclusion chromatography

|  | Molecular weight | Elution time (min.) | Degree of polymerization |
|---|---|---|---|
| P-20 | 23,700 | 22.6 | 150 |
| P-10 | 12,200 | 24.3 | 75 |
| P-5 | 5,800 | 26.6 | 35 |
| Dissolved precipitate sample | 11,400 | 24.7 | 70 |

4. Sugar Composition and Type of Bond

When the sugar composition analysis of the precipitate was performed, the monosaccharide constituting the polysaccharide was only glucose. Accordingly, it was revealed that the precipitate was a polymer of glucose.

Figure 2:
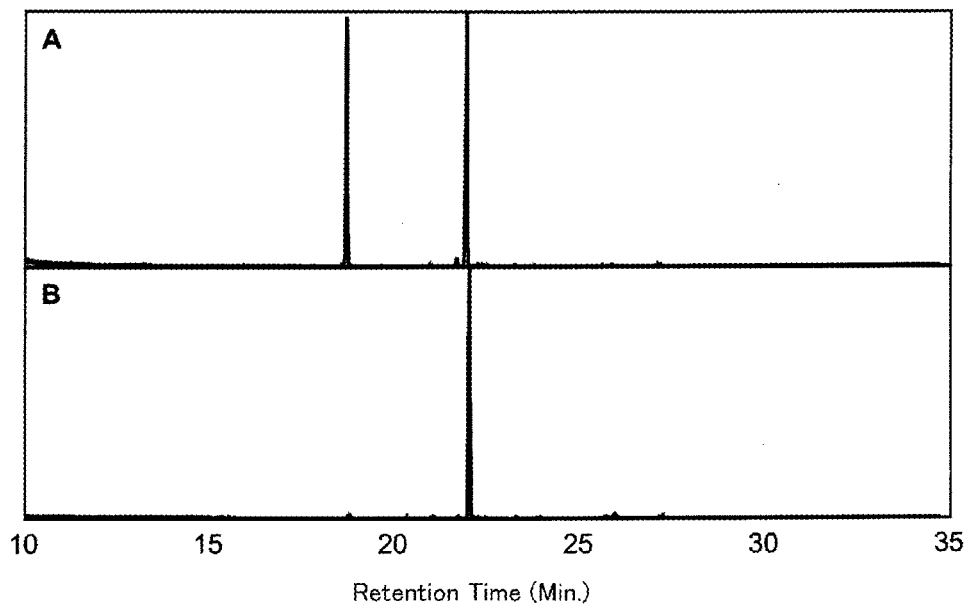
FIG. 2 is a GC-MS chromatogram of a partially methylated alditol acetate (PMAA). It shows the results achieved when a methylated carbohydrate was subjected to GC-MS after having been acid-hydrolyzed and acetylated. The upper side (A) shows the results of laminaribiose serving as a standard product, and the lower side (B) shows the results of the precipitate.
Figure 3:
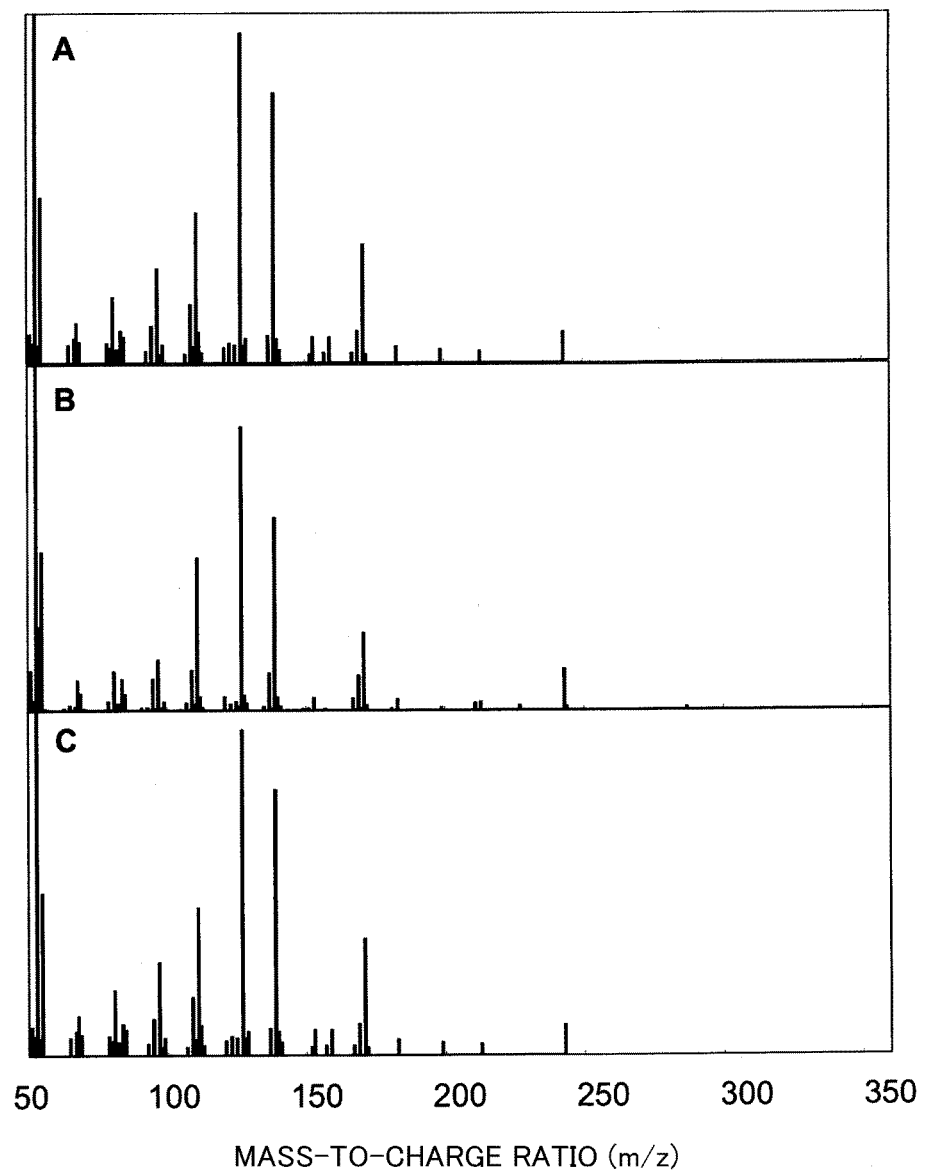
FIG. 3 is a mass spectrum of a partially methylated alditol acetate. The top (A) shows the spectrum of 1,3,5-tri-o-acetyl-2,4,6-tri-o-methyl hexitol (GC-MS library) serving as the standard product, the middle (B) shows the spectrum of the peak at 22.0 minutes of FIG. 2A (the sample used for the methylation analysis of the laminaribiose), and the lowest (C) shows the spectrum of the peak at 22.0 minutes of FIG. 2(B) (the sample used for the methylation analysis of the precipitate).

A methylation analysis was carried out to determine the type of bonds between the monosaccharides of the precipitate (enzymatically-synthesized polysaccharide). When a partially methylated alditol acetate obtained from the precipitate was subjected to GC-MS, a peak was observed at the position of the retention time of 22.0 minutes (FIG. 2). Furthermore, when a partially methylated alditol acetate, which was obtained from laminaribiose having beta-1,3-linkages and glucose serving as the constituent sugar, was subjected to GC-MS, a peak was also observed at the same retention time. These mass spectra corresponded to 1,3,5-tri-o-acetyl-2,4,6-tri-o-methylhexytol of the GC-MS library (FIG. 3). Therefore, it was revealed that 1,3-glucosidic bonds were present in the precipitate. Other than the aforementioned peak at 22.0 minutes, a large peak was not observed in the samples obtained from the precipitate. Almost no 1,5-di-o-acetyl-2,3,4,6-tetra-o-methyhexytol (retention time: 18.8 min), which is derived from the non-reducing end and detected in the sample from laminaribiose, was detected in the samples resulting from the precipitate. Accordingly, the precipitate is considered to be a linear 1,3-glucan having a high degree of polymerization.

Figure 4:
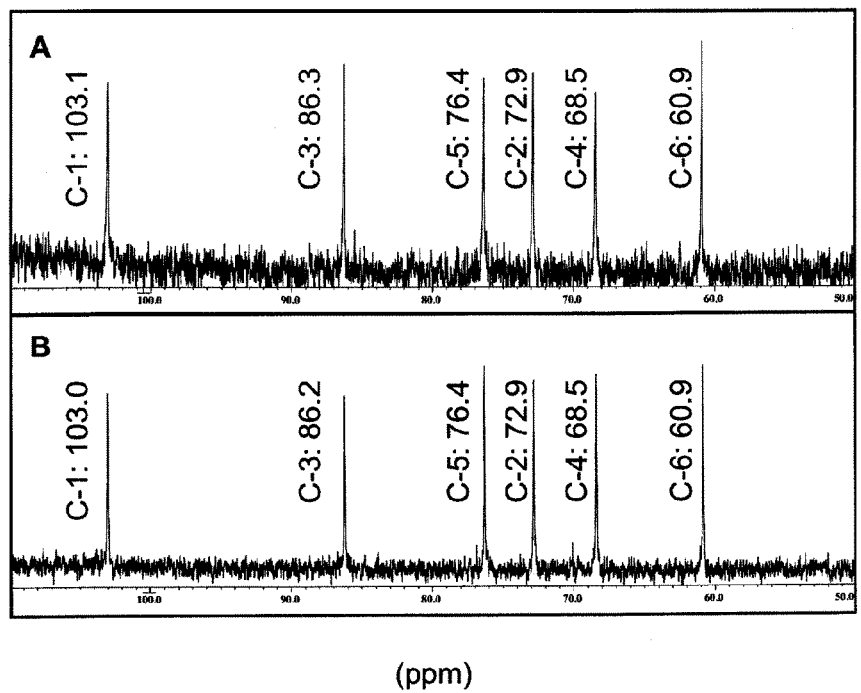
FIG. 4 is a $^{13}$C-NMR spectrum. The upper (A) shows the results of curdlan (polysaccharide having beta-1,3-glucosidic bonds) and the lower (B) shows the results of the precipitate.

Furthermore, the precipitate and curdlan, which is a polysaccharide having beta-1,3-glucosidic bonds, have the same $^{13}$C-NMR spectrum (FIG. 4). Therefore, it was revealed that the precipitate is a linear beta-1,3-glucan.

5. Synthesis of the beta-1,3-glucan Using Highly-Purified Enzyme

Figure 5:
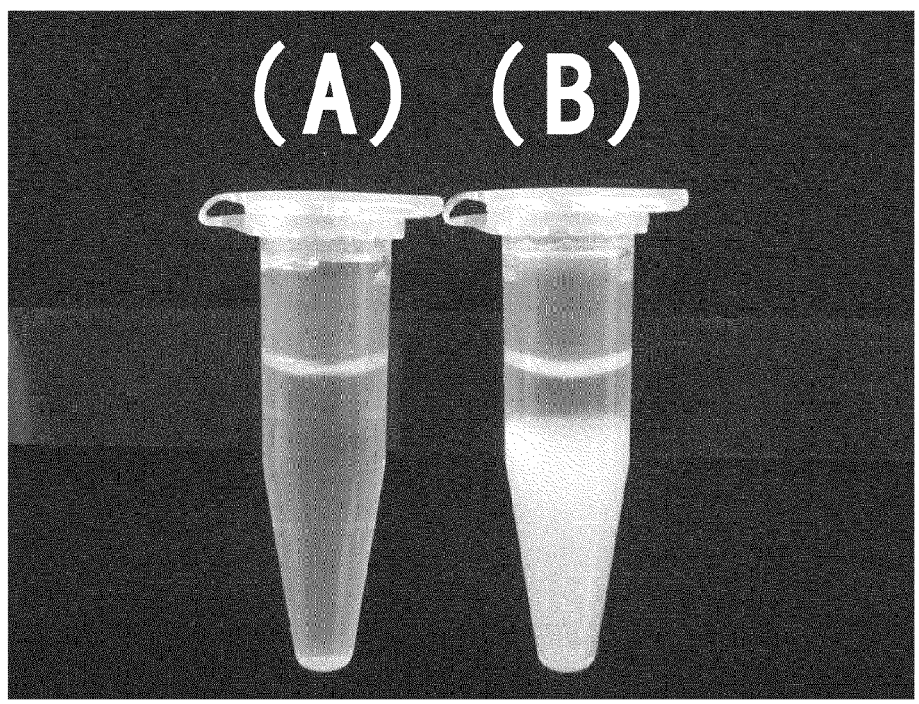
FIG. 5 is a photograph taken at a time that confirmed the state of forming the precipitate when the highly-purified enzyme was used. The left side (A) shows the reaction solution when a primer (laminaripentaose) was not added, and the right side (B) shows the reaction solution when a primer (laminaripentaose) was added. Precipitation of polysaccharide was observed in (B).

In FIG. 5, the results of a synthesis study of beta-1,3-glucan using highly purified enzymes are shown. As was described above, when a crude enzyme is used, beta-1,3-glucan can be synthesized without the addition of a primer. As shown in FIG. 5, however, beta-1,3-glucan was not synthesized without the addition of a primer when a highly purified enzyme was used. On the other hand, synthesis of beta-1,3-glucan was observed when a primer (in this case, laminaripentaose) was added to the reaction solution. Thus, when highly purified beta-1,3-glucan phosphorylase is used, it is considered necessary to add a primer during the reaction.

6. Influence of the Reaction Temperature

Synthesis of beta-1,3-glucan was confirmed when the reaction temperature ranged from 20° C. to 50° C., as shown in TABLE 2. The precipitate yield differs depending upon the temperature; it ranges from 30% to 60% when the reaction temperature is at or below 45° C. The molecular weight distribution differs depending upon the reaction temperature; peaks were observed in a range of relatively lower molecular weights from 6,000 to 6,500 (degree of glucose polymerization from 35 to 40) when the reaction temperature is at or above 40° C.

TABLE 2

Relationship between reaction temperature, product yield and molecular weight

| Reaction Temperature (° C.) | Precipitate Yield (%) | Molecular Weight (peak) | Degree of polymerization |
|---|---|---|---|
| 20 | 53.1 | 8,900 | 55 |
| 25 | 57.3 | 9,900 | 60 |
| 30 | 55.2 | 11,000 | 70 |
| 35 | 45.9 | 11,000 | 70 |
| 40 | 36.4 | 6,200 | 40 |
| 45 | 32.4 | 6,400 | 40 |
| 50 | 2.4 | not-analyzed | not-analyzed |
| 55 | 0.0 | not-analyzed | not-analyzed |

7. Influence of pH

Synthesis of beta-1,3-glucan was confirmed at a pH ranging from 4.4 to 7.8 at the time that the reaction was terminated, as shown in TABLE 3. The precipitate yield differs depending upon the pH and is higher in the pH range of pH5~pH7. The molecular weight distribution differs depending upon the reaction pH. Peaks were observed at locations of relatively short molecules when the reaction pH was low.

TABLE 3

Relationship between reaction pH, product yield and molecular weight

| pH at the start of the reaction | pH at the end of the reaction | Precipitate yield (%) | Molecular weight (peak) | Degree of polymerization |
|---|---|---|---|---|
| 3.9 | 3.9 | 0.0 | not-analyzed | not-analyzed |
| 4.4 | 4.4 | 29.3 | 5,800 | 35 |
| 5.1 | 5.3 | 63.2 | 10,600 | 65 |
| 5.8 | 6.2 | 61.2 | 10,600 | 65 |
| 6.6 | 7.1 | 49.3 | 11,000 | 70 |
| 7.3 | 7.8 | 41.5 | 11,000 | 70 |

8. Influence of the G1P Concentration

Synthesis of beta-1,3-glucan was confirmed when the final concentration of G1P was not less than 10 mM, as shown in TABLE 4. Although the precipitate yield differs depending upon the G1P concentration, the molecular weight distribution is substantially the same.

TABLE 4

Relationship between G1P concentration, product yield and molecular weight

| G1P final concentration (mM) | Precipitate yield (%) | Molecular weight (peak) | Degree of polymerization |
|---|---|---|---|
| 10 | 4.9 | not-analyzed | not-analyzed |
| 25 | 15.1 | 10,600 | 65 |
| 50 | 34.3 | 11,000 | 70 |
| 100 | 48.1 | 11,000 | 70 |
| 200 | 56.5 | 11,000 | 70 |
| 400 | 38.1 | 10,600 | 65 |

9. Influence of the Amount of Enzyme

Figure 6:
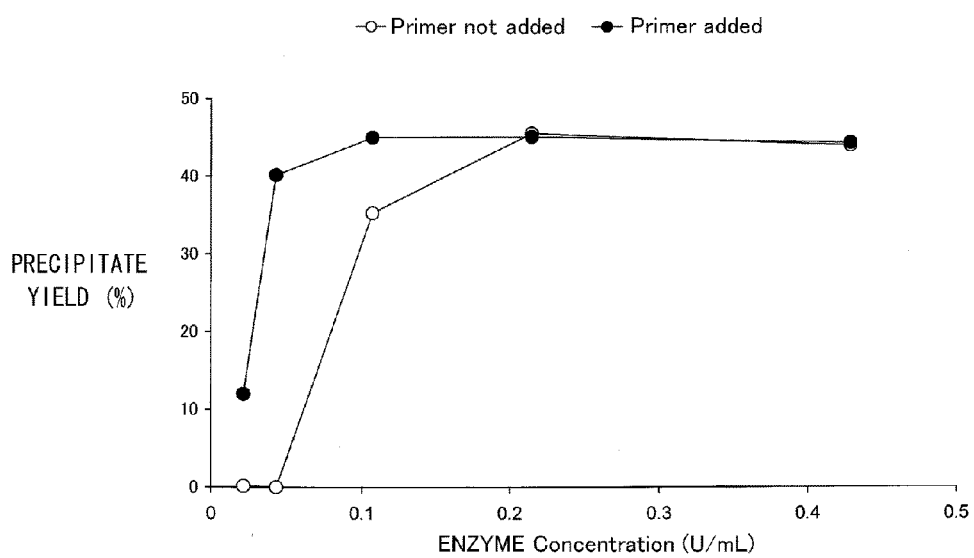
FIG. 6 is a graph showing results, which confirmed the influence that changes in the amount of enzyme impart on the product yield. In case a small amount of enzyme was used, a precipitate was not obtained when a primer was not added (O), but the formation of a precipitated was confirmed when a primer was added (●).

In FIG. 6, the results of an analysis of the influence of the amount of enzyme are shown. Precipitate formation was observed when no laminarioligosaccharide (primer) was added and the amount of enzyme was not less than 0.1 U/mL (final concentration). Thus, when the crude enzyme is used, beta-1,3-glucan can be synthesized without the use of a primer. Precipitate formation was not observed when the amount of enzyme was not more than 0.04 U/mL. On the other hand, in case a small amount of laminarioligosaccharide (primer) was added, precipitate formation at high yield was observed even though the amount of enzyme was at 0.04 U/mL. Furthermore, precipitate formation was observed even though enzyme having an even lower concentration was used. Thus, in case laminarioligosaccharide (primer) is added, it was revealed that beta-1,3-glucan can be synthesized even though the amount of enzyme content is low.

10. Influence of the Amount of Primer

Figure 7:
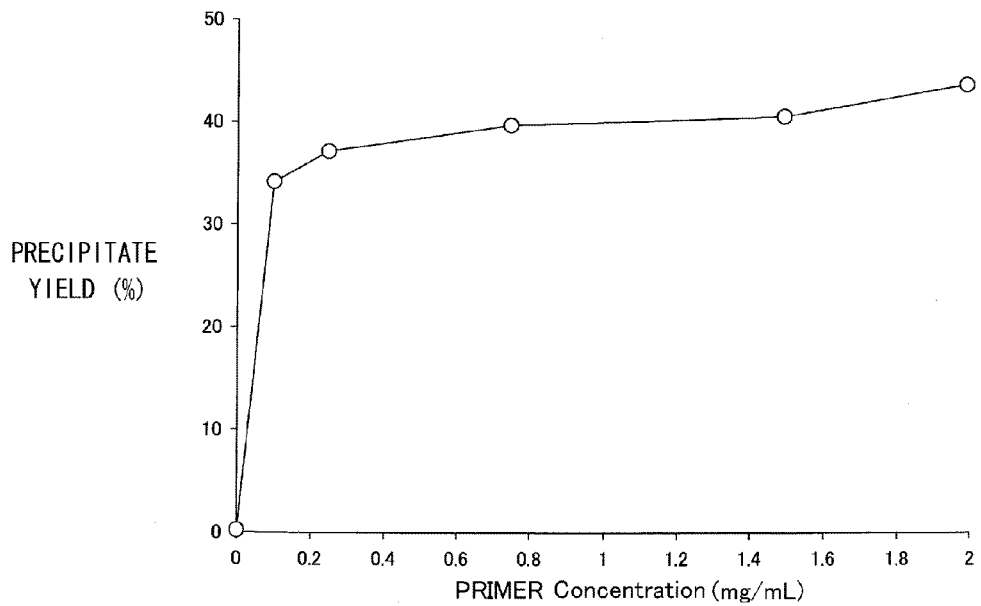
FIG. 7 is a graph showing results, which confirmed the influence that changes of the primer concentration impart on the product yield. By adding not less than 0.1 mg/mL (final concentration) of primer, the formation of a precipitate in a high yield was confirmed in spite of the small amount of enzyme.

In FIG. 7, the results of an analysis of the influence of the amount of primer are shown. Since only a small amount of enzyme was added to the reaction system, no precipitate is produced when no primer was added, as shown in the results of <9. Influence of the amount of enzyme>. On the other hand, by adding 0.1 mg/mL (final concentration) of primer, the formation of precipitate in high yields was confirmed. Thus, in case a small amount of enzyme is used, it was revealed that the yield of the beta-1,3-glucan can greatly be increased by the addition of a small amount of primer.

11. Influence of the G1P Concentration when Primer is Added

Figure 8:
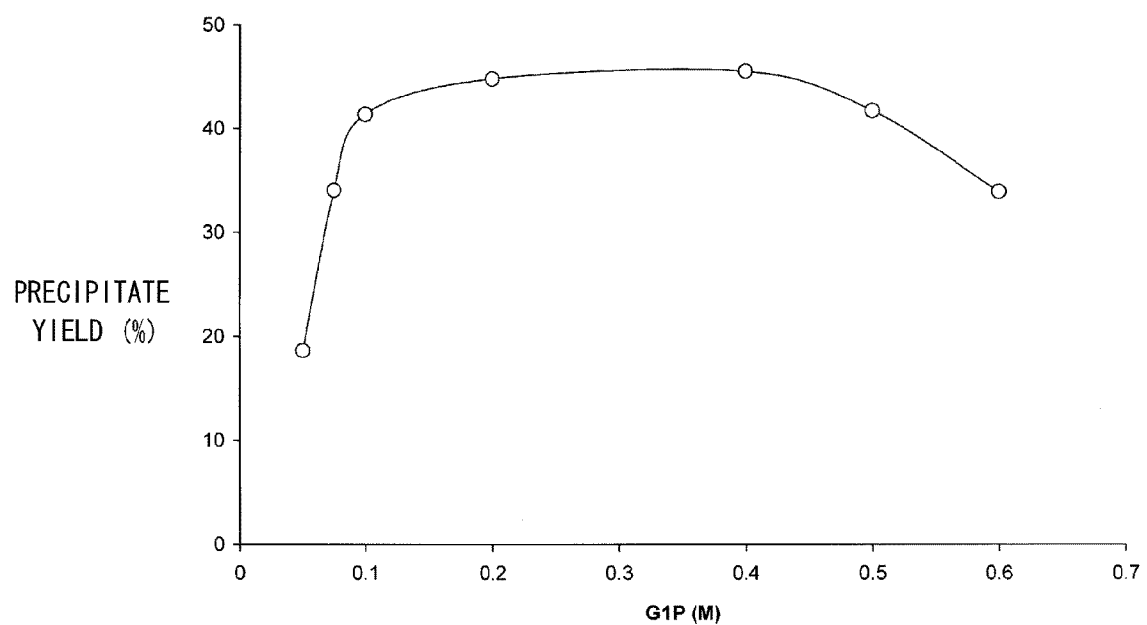
FIG. 8 is a graph showing results, which confirmed the influence that the G1P concentration imparts when primer is added. Synthesis of beta-1,3-glucan was observed within the range of 0.05 M~0.6 M G1P; more particularly, it was confirmed that the synthesis yield of beta-1,3-glucan was high within the range of 0.1 M~0.5 M G1P.

In FIG. 8, the results of analysis of the influence of the G1P concentration when primer is added are shown. Synthesis of beta-1,3-glucan was carried out with variations in the G1P concentration in the presence of a small amount of laminarioligosaccharide (primer). Synthesis of beta-1,3-glucan was confirmed in the range of 0.05 M~0.6 M G1P. It is particularly obvious that the synthesis yield of beta-1,3-glucan is high in the range of 0.1 M~0.5 M G1P.

Thus, according to the foregoing embodiments, beta-1,3-glucan having a degree of polymerization of several tens (on the order from 30 to 70) can easily be manufactured.

The invention claimed is:

1. A method for manufacturing a linear-chain beta-1,3-glucan, comprising:
   polymerizing glucose-1-phosphate serving as a substrate by contacting the glucose-1-phosphate with a beta-1,3-glucan phosphorylase derived from a species in the genus *Ochromonas* and with a laminarioligosaccharide serving as a primer, thereby forming the linear-chain beta-1,3-glucan.

2. The method according to claim 1, wherein the beta-1,3-glucan phosphorylase is derived from *Ochromonas danica*.

3. The method according to claim 1, wherein the pH during the polymerization reaction is between 4 and 8.

4. The method according to claim 1, wherein the concentration of glucose-1-phosphate during the polymerization reaction is between 0.01 M and 0.6 M.

5. The method according to claim 1, wherein the temperature during the polymerization reaction is between 20° C. and 45° C.

6. The method according to claim 5, wherein the beta-1,3-glucan phosphorylase is derived from *Ochromonas danica*, the pH during the polymerization reaction is between 4 and 8, and the concentration of glucose-1-phosphate during the polymerization reaction is between 0.01 M and 0.6 M.

7. The method according to claim 6, wherein the linear beta-1,3-glucan has a degree of polymerization between 30 to 70.

8. The method according to claim 1, wherein the linear beta-1,3-glucan has a degree of polymerization between 30 to 70.

9. The method according to claim 7, wherein the laminarioligosaccharide has a degree of polymerization between 2 and 20.

10. The method according to claim 7, wherein the laminarioligosaccharide is laminaribiose or laminaripentaose.

11. The method according to claim 9, wherein the initial concentration of laminarioligosaccharide is between 0.1 and 2 mg/mL.

12. The method according to claim 11, wherein the initial pH during the polymerization reaction is between 5.1 and 7.3 and the concentration of glucose-1-phosphate is between 0.1 M and 0.5 M.

13. The method according to claim 1, wherein the laminarioligosaccharide has a degree of polymerization between 2 and 20.

14. The method according to claim 1, wherein the laminarioligosaccharide is laminaribiose or laminaripentaose.

15. A method for manufacturing a linear-chain beta-1,3-glucan containing only beta-1,3-bonds, comprising:
polymerizing glucose-1-phosphate serving as a substrate by contacting the glucose-1-phosphate with a beta-1,3-glucan phosphorylase derived from a species in the genus *Ochromonas* and with a laminarioligosaccharide containing only beta-1,3-bonds and serving as a primer, thereby forming the linear-chain beta-1,3-glucan containing only beta-1,3-bonds.

16. The method according to claim 15, wherein the laminarioligosaccharide has a degree of polymerization between 2 and 20 and the linear beta-1,3-glucan has a degree of polymerization between 30 to 70.

17. The method according to claim 16, wherein the beta-1,3-glucan phosphorylase is derived from *Ochromonas danica*.

18. The method according to claim 17, wherein the laminarioligosaccharide is laminaribiose or laminaripentaose.

* * * * *